(12) United States Patent
Brinton et al.

(10) Patent No.: US 6,391,262 B1
(45) Date of Patent: May 21, 2002

(54) TEST KIT FOR MEASURING VOLATILE AMMONIA IN BIOLOGICAL SAMPLE

(76) Inventors: William F. Brinton; Eric Evans, both of Rte. 2, Box 1850, Mount Vernon, ME (US) 04352

( * ) Notice: Subject to any disclaimer, the term of this patent is extended or adjusted under 35 U.S.C. 154(b) by 0 days.

(21) Appl. No.: 09/375,038

(22) Filed: Aug. 16, 1999

(51) Int. Cl.[7] .............................................. G01N 33/48
(52) U.S. Cl. ........................ 422/61; 422/58; 436/164; 436/166; 436/169
(58) Field of Search ........................... 422/56, 58, 61; 436/113, 164, 168, 166, 169

(56) References Cited

U.S. PATENT DOCUMENTS

| | | | | |
|---|---|---|---|---|
| 4,409,182 A | * | 10/1983 | Macklem | 422/61 |
| 5,308,771 A | * | 5/1994 | Zhou et al. | 436/166 |
| 5,514,639 A | * | 5/1996 | Fisher et al. | 504/116 |
| 5,976,467 A | * | 11/1999 | Dallas et al. | 422/86 |

* cited by examiner

Primary Examiner—Lyle A. Alexander
(74) Attorney, Agent, or Firm—Frederick R. Cantor, Esq.

(57) ABSTRACT

A test kit for determining the "volatile ammonia content" of biological samples comprising any wet or dry compost, manure, plasma or soil sample. The kit includes a transparent container for holding the sample, and a reactant chemistry gel system, located within the container in the space not occupied by the sample. The reactant mass includes an acidic pH reactant material, and a color change indicator material, responsive to pH changes in the reactant material. Ammonia vapors diffuse into the reactant material, reacting chemically with the acidic pH reactant material so as to produce a color change. The nature of the color change is an indication of the quantity of $NH_3$ in the test-jar atmosphere, which in combination with the known pH of the sample, indicates the total ammonium in the biological sample.

8 Claims, 4 Drawing Sheets

TEST KIT FOR MEASURING VOLATILE AMMONIA IN BIOLOGICAL SAMPLE

BACKGROUND OF THE INVENTION

Ammonia is toxic to plants when present at elevated amount in fertilizer and composts. Ammonia in any amount is toxic to fish. In beer and wine samples, ammonia spoils the flavor qualities. Ammonia in the air is odorous and hazardous to health. In soils ammonia can be measured to help maintain nutrient balance.

The present invention relates to test kits that can be used to determine the volatile ammonia content, indicative of the chemical nitrogen stability of a selected sample. The test is especially intended for manures, feces, compost or solid organic waste and other biological samples including soil, beer pulp and water and air. The test kit comprises a first reactant mass, that exhibits a color change in the presence of varying quantities of ammonia ($NH_3$), whereby the test kit can be used to test for the ammonia gas content in a compost sample, and indirectly the total ammonium. The test kit is especially designed for use by operators of facilities where digested sludge, leaves, manure, and other waste products, are being processed or transformed into useful compost, having value as a natural fertilizer. The test kit may also enable operators of animal facilities to determine the level of ammonia gas likely to be produced in confined quarters, since ammonia gas has a negative impact on animal health and worker safety. Ammonia determined as a volatile gas from low levels of $NH_3$ gas in a compost sample is indicative of a state of "maturity" or completion of the compost process.

Composting is a process of biological oxidation of organic materials, e.g., digested sludge, leaves, etc., whereby the materials are dewatered and deodorized into a finely divided condition, suitable for use as a fertilizer. The composting operation can be carried out by either a windrow-composting procedure, an in-vessel procedure, a back-yard bin procedure, or a static pile composting procedure.

In a composting procedure, waste products are formed into elongated or conical piles. Periodically, a composting machine is employed to rotate, to lift, mix, and shred the organic materials, so that materials near the outer surface of the windrow, exchange places with materials in the interior zone of the windrow. With compost processing of manures and other wastes, normally a period of between two (2) and twelve (12) weeks of biological activity is required to bring the materials to a stable condition at which point there is little if any residual ammonia content.

The production of ammonia gas by the breakdown of proteinaceous (high-nitrogen) materials is a normal process in all decomposition and even in fermentation processes. The evolution and evaporation of ammonia gas in composting or from waste piles is governed by the ratio of total carbon to total nitrogen (C:N ratio) in the initial compost blend. In soil the release of ammonia from urea or ammonium salt fertilizers is governed by the pH. Nitrogen is prevalent in all proteinaceous materials, such as manure, urine, fresh plant and animal materials, waste-water treatment solids (biosolids), fermentation broths and wastes, food wastes, animal feeds, etc. It is a goal of fertilizer manufacture and composting to balance the carbon, nitrogen and pH so as to limit loss as free gas vapor $NH_3$. If nitrogen is present in excess of the needs of micro-organisms in compost or soil, the surplus will accumulate and/or evaporate in the form of ammonia gas.

The accumulation and evaporation of ammonia gas is strongly affected by the pH of the compost or other medium present. Ammonia production in compost always occurs in an aqueous (water) medium, moist bio-films on the compost particles in which the micro-organisms are active. In the presence of water, the chemical form of ammonia is described by the following equation:

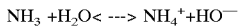

$$NH_3 + H_2O \longleftrightarrow NH_4^+ + HO^-$$

Increasing pH is associated with increasing $HO^-$ (hydroxide ion), which shifts the equilibrium to the left, increasing the proportion or concentration of $NH_3$ (ammonia gas). Conversely a low pH is associated with low $HO^-$, which shifts the equilibrium to the right, decreasing the amount of volatile ammonia gas present. Ammonia gas is very volatile and therefore tends to diffuse into the gaseous medium surrounding the compost or soil and other particles and the atmosphere above the sample in the test kit.

The significance of ammonia content in compost is different for different compost end-use applications. Ammonia gas can be quite odorous and unpleasant and is rated as an irritant. Ammonia in "hot" or unstable manures and composts can be phytotoxic, inhibiting seed germination and causing "burning" or yellowing of plant foliage when applied to soil. The presence of a high $NH_3$ gas content in the compost materials indicates that the composting process is incomplete, and that the material is biologically unstable. However, a high test result for volatile $NH_3$ content may also indicate that a compost would be an excellent source of soluble nitrogen (ammonia) fertilizer in some applications where phytotoxicity is not expected. The present invention relates to low cost test kits, that can be used by the facility operator to determine approximately the volatile ammonia content, whereby the operator can then make an informed decision as to controlling the C:N ratio or pH of the materials to reduce ammonia levels, or otherwise changing or ending the treatment process parameters.

BRIEF SUMMARY OF THE INVENTION

The primary object of the present invention is to provide test kits that can be used to determine the "volatile ammonia content" and chemical stability of a selected biological sample. The test kit comprises a first reactant mass, that exhibits a color change in the presence of varying quantities of ammonia ($NH_3$), whereby the test kit can be used to test for the ammonia $NH_3$ content in a compost or manure or fertilizer sample. The present invention contemplates a test kit for determining the volatile ammonia content and nitrogen-stability of a moist biological sample. The test kit comprises a small container, or jar, adapted to contain, and fully enclose, a small compost or manure or other sample, whereby $NH_3$ gas emitted by the sample is trapped within the container. A reactant mass is supported within the container, so as to be in contact with the emitted gases, said reactant mass comprising an acidic medium that acts as a "sink" for ammonia, thereby drawing it out of the air, and a color change compound, responsive to pH changes in the reactant mass.

The jar is left undisturbed for a period of time, e.g., about three to four (3–4) hours, during which time $NH_3$ gas diffuses out of the sample and into the reactant mass. The amount of ammonia gas that diffuses into the reactant mass is proportional to the ammonia gas concentration in the compost sample. Chemical reactions occurring in the reactant material are visibly recorded as a color change in the color change material. Therefore the extent of color change is proportional to the ammonia gas concentration in the sample.

In summary, and in accordance with the above discussion, the foregoing objectives are achieved in the following embodiments.

1. A test kit for determining the volatile ammonia concentration of a biological sample comprising:

a container;

said container having a transparent side wall, and an open end;

a reactant support tab;

a reactant mass carried by said reactant support tab, said reactant mass comprising an acidic pH reactant material, and a color change indicator material; and a cover removably and sealably engaged on said open end of said container;

whereby the color of said reactant mass may be observed through said transparent side wall of said container.

2. The test kit for determining the volatile ammonia concentration of a biological sample, as described in paragraph 1, wherein said color change indicator material undergoes color changes in the pH range from about 3 to about 9, whereby said test kit can be used to test for volatile ammonia content in said container.

3. The test kit for determining the volatile ammonia concentration of a biological sample, as described in paragraph 1, wherein the said acidic pH reactant material comprises potassium-hydrogen-phthalate.

4. The test kit for determining the volatile ammonia concentration of a biological sample, as described in paragraph 1, wherein said color change indicator material comprises a first substance undergoing a color change in the pH range from about 3 to about 6, and a second substance, undergoing a color change in the pH range from about 7 to about 9, whereby said material has a range of colors from yellow to blue, depending on the pH.

5. The test kit for determining the volatile ammonia concentration of a biological sample, as described in paragraph 1, wherein said reactant support tab further comprises;

a flat blade, having a relatively shallow recess therein;

said reactant mass being located within said recess;

a handle to facilitate insertion of said tab into said container without touching said reactant mass;

whereby said blade allows for insertion into, and self-standing within, a biological sample within said container.

6. The test kit for determining the volatile ammonia concentration of a biological sample, as described in paragraph 5 wherein said shallow recess has a depth of about two (2) millimeters; and said reactant mass, being a flat patch of material filling said recess, whereby said patch has a thickness of no more than about two (2) millimeters; the surface of said recess being etched to better adhere said reactant mass.

7. The test kit for determining the volatile ammonia concentration of a biological sample, as described in paragraph 1, wherein said reactant mass has a face area of about one (1) square inch.

8. The test kit for determining the volatile ammonia concentration of a biological sample, as described in paragraph 1, wherein said reactant support tab is inserted a biological sample so that the reactant mass is in a container space not occupied by the said biological sample and not directly in contact with said biological sample.

9. The test kit for determining the volatile ammonia concentration of a biological sample, as described in paragraph 1, wherein said reactant mass further comprises an inert carrier material; said reactant material and said color change indicator material being uniformly dispersed within said carrier material.

10. The test kit for determining the volatile ammonia concentration of a biological sample, as described in paragraph 9, wherein said carrier material is agar gel.

11. The test kit for determining the volatile ammonia concentration of a biological sample, as described in paragraph 1, wherein said biological sample is a liquid having a pH increased to 11.0.

12. A test kit for determining the volatile ammonia concentration of a surrounding environment comprising:

a container;

said container having a transparent side wall, and an open end;

a reactant support tab;

a reactant mass carried by said reactant support tab, said reactant mass comprising an acidic pH reactant material, and a color change indicator material; and a gas permeable cover removably engaged on said open end of said container;

whereby the color of said reactant mass may be observed through said transparent side wall of said container.

DETAILED DESCRIPTION OF THE INVENTION

Figure 1:
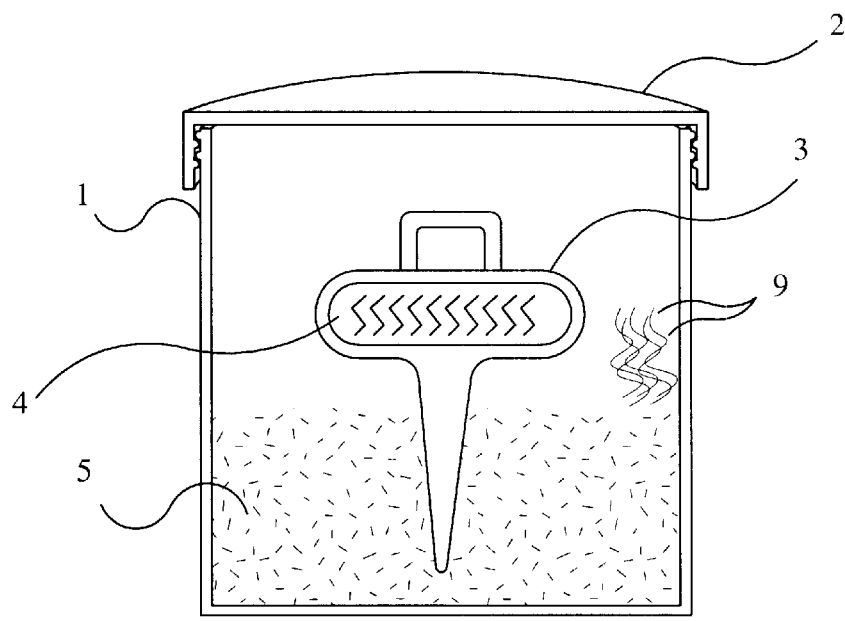
FIG. 1, is a sectional view, taken through a test kit, constructed according to the present invention.

This invention relates generally to a commonly owned, and previously issued U.S. Pat. No. 5,320,807, "Test Kits for Determining the Chemical Stability of a Compost Sample." The present invention pertains to an improvement of the previous invention wherein this new test kit invention is useful in detection of ammonia content of a biological sample. The prior art invention is directed to the detection of carbon dioxide gas as a means of determining the chemical stability of a compost sample.

As noted previously, the present invention relates to a low cost test kit that can be used to determine the ammonia content of a biological sample. Each test kit construction includes a container for holding the biological sample, and a reactant mass, comprising an acidic pH reactant material, e.g. KHP (potassium-hydrogen-phthalate, also known as potassium biphthalate, phthalic acid, potassium salt, potassium acid phthalate) buffer, and a color change material, responsive to pH changes in the reactant material. The container has a transparent wall, whereby color changes in the indicator material can be observed, without opening the container, or removing the reactant mass.

The reactant mass may be a thin patch of material, supported on a tab, blade, or paddle, placed within the transparent container, such that the colored patch can be readily seen through the transparent container wall. The test kit is designed to measure the rate of release of ammonia gas from a moist compost or other biological sample, in a prescribed period of time, e.g. two to four (2–4) hours from the time that the biological sample is inserted into the container. The test is useful for compost producers who need to determine when a compost is finished and ready for market, i.e., when the compost is biologically stable or non-harmful. In the test container, the ammonia gas ($NH_3$) diffuses from the compost sample into an agar gel carrier for an acidic pH reactant material, and a pH responsive color change material. The ammonia gas is trapped in the agar gel, resulting in a visual color change, due to the neutralization of the acidic buffer. The ammonia test contributes to understanding the total compost maturity. The more advanced the composting process is, the less ammonia is observed. Information on ammonia content aids in deciding when true biological maturity has been reached. Such information also can be used to estimate the nitrogen content, and the value of the compost as a fertilizer, or to predict potential danger from overly high ammonia in the sample, such as in chicken manure, water from waste processing or fermentation batches and in fertilizers and composts.

Color changes are produced in two pH color change substances, dispersed with the agar gel carrier matrix. In a preferred test kit construction, two pH indicators are used. One color change substance is bromocresol green, which has a color change range from yellow to blue in the pH range of about 3 to about 6. The second color change substance is thymol blue, having a color change from yellow to blue in the pH range from about 7 to about 9. When the two color change substances are combined, the color changes overlap, so as to provide a continuous range of colors from yellow to green to blue, depending on the pH. At a pH of about 6–7, the blue of the bromo-cresol green combines with the yellow from the thymol blue, to produce green.

When used in conjunction with the prior art carbon dioxide test kit, i.e., both tests conducted concurrently with the same sample in one container, the new test kit reactant material improves the accuracy and response of the carbon dioxide test. The ammonia gas emitted from a compost sample is absorbed by the new inventive element thereby minimizing the effect of any ammonia gas effect on the carbon dioxide test.

FIG. 1, is a sectional view, taken through a test kit, constructed according to the present invention.

Figure 2:
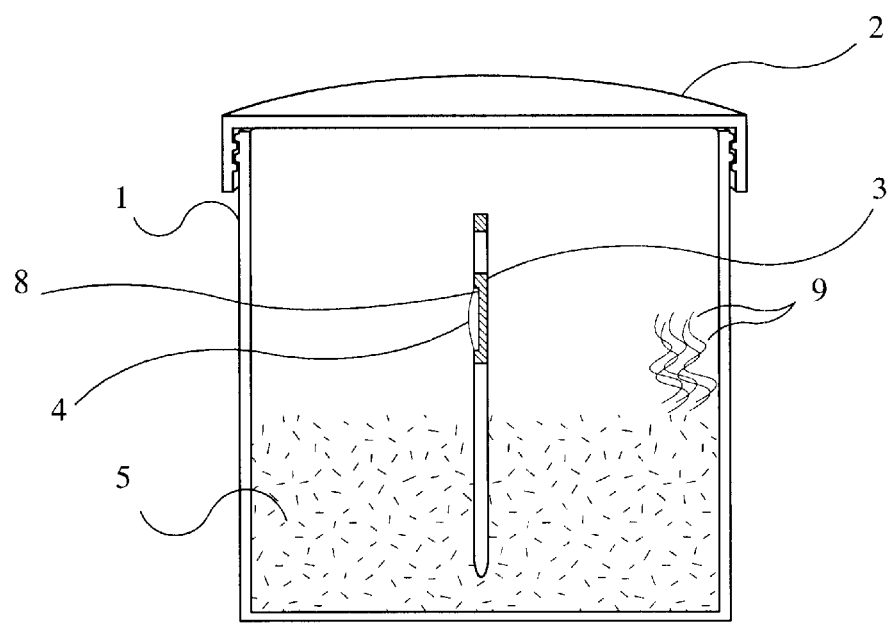
FIG. 2 is a side sectional view, taken through a test kit, constructed according to the present invention.

FIG. 2, is a side sectional view of the same test kit as represented in FIG. 1.

FIG. 1 and FIG. 2 show a test kit embodying the present invention. A cylindrical container 1, is formed of a transparent plastic material, whereby the container interior space is readily seen through the transparent container side wall. The mouth of the container is threaded to receive a cover, 2. With the cover 2, removed, a sample 5, of biological matter can be inserted into the container 1. A pre-determined quantity of biological matter e.g. compost or fertilizer, is used; approximately 100 cc. For convenience, a fill-line may be provided on the container 1, to measure the sample quantity on a volume basis.

Figure 4:
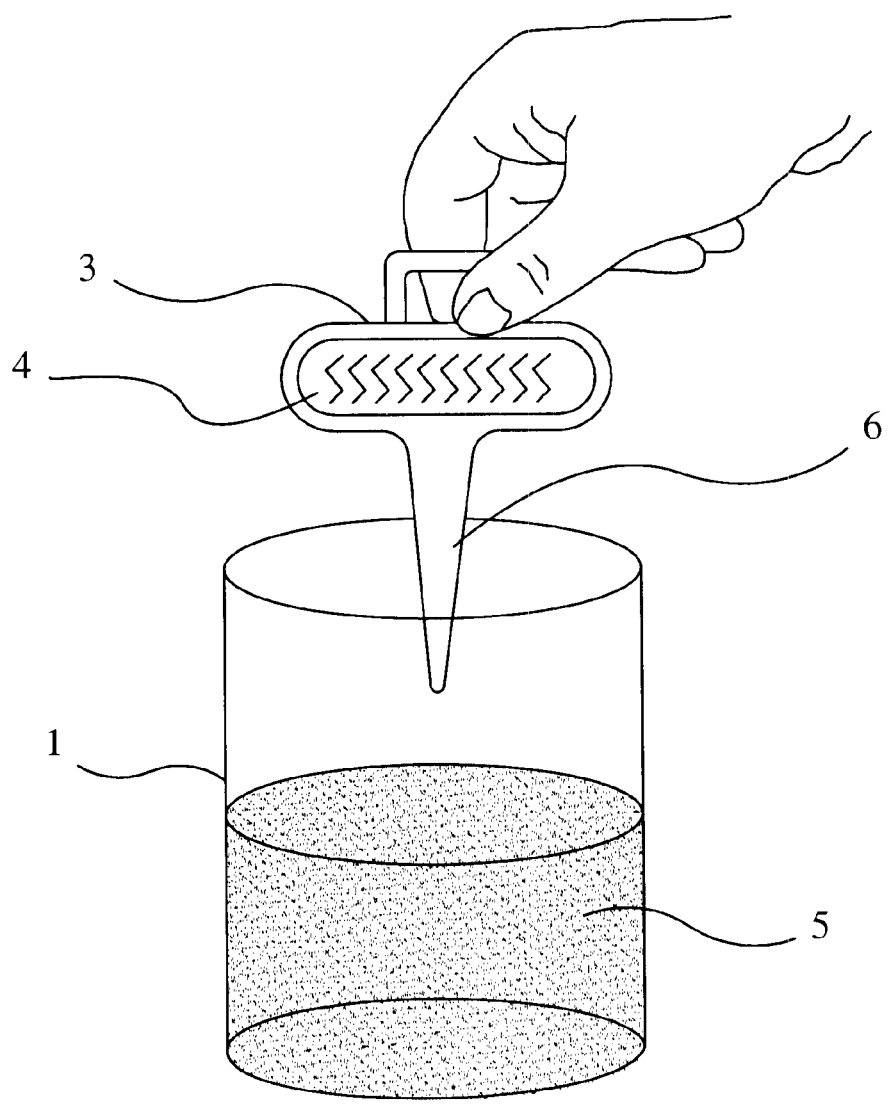
FIG. 4, is an assembly view of the test kit, with the cover removed.

FIG. 4 is an assembly view of the test kit being assembled with container 1 appropriately filled with a biological sample. A plastic reactant support tab 3 having a blade 6, is inserted into the biological sample so that the reactant material is in the space not occupied by the compost sample 5.

Referring back to FIG. 2, a shallow recess 8, is formed in the flat side surface of reactant support tab 3, to form a receptacle for a reactant mass 4. Typically, recess 8, will have a depth of about two (2) millimeters, i.e., about eight-hundredths (0.08) of an inch. The reactant mass 4, will completely fill the recess 8, so that the surface of the reactant mass 4, is co-planar with the reactant support tab 3 surface. The thin reactant patch 4, has a relatively large exposed surface area to volume ratio, whereby reaction with the ammonia gas 9 is facilitated. The exposed surface area of the patch, as viewed in FIG. 1 may; be about one (1) square inch.

Reactant patch 4, may be formed by pouring a heated reactant mixture into recess 8, using the recess 8 as a mold cavity. The reactant mixture can be prepared by a series of steps that includes adding the agar to the KHP buffer solution and heating it to the boiling point. Minor quantities of thymol blue and bromo-cresol green are added to the above solution. A preservative such as benzalkonium chloride and propylparaben, or equivalents, can be added to prevent bacterial growth during storage. The heated mixture is then immediately poured into the mold cavity, i.e., recess 8, as seen in FIG. 2, and allowed to harden.

Figure 3:
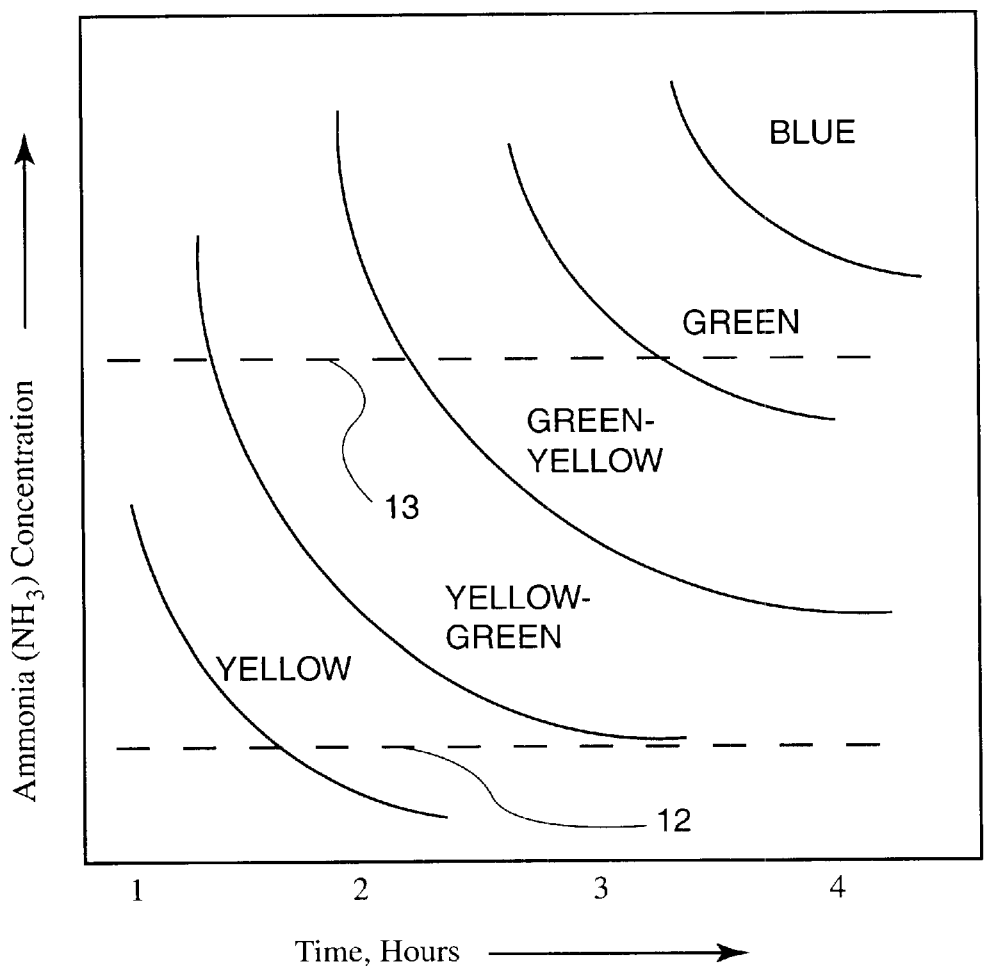
FIG. 3, is a chart, illustrating the performance of the test kit, depicted in FIGS. 1 and 2.

FIG. 3 is a chart, illustrating the performance of the test kit, depicted in FIG. 1. The test kit operates empirically, on the basis of calibration work, run with known material compositions, i.e, known compost or fertilizer ammonia contents. FIG. 3, shows graphically how the test kit performs. The graph shown there plots the color of the color indicator versus elapsed time in the test, for four different compost samples with different ammonia contents. Initially, the reactant patch 4, will have a yellow color. As the container is allowed to remain undisturbed for a period of time, the coloration of the patch may change, depending on the quantity of ammonia emitted from the sample being tested. The sample represented by line 12 in FIG. 3 remains yellow, indicating a relatively low concentration of ammonia in the sample. By comparison, the sample represented by line 13 represents a sample having a higher concentration of ammonia resulting in the reactant patch changing to shades of increasingly green color.

The presence of ammonia in significant amounts is an indicator of biological instability or immaturity of compost. On a parts-per-million basis, ammonia levels can be classified generally as follows:

TABLE 1

| ppm $NH_3$ of sample | Fertilizer/Compost Quality | Color, at pH 8 | Color, at pH 9 |
| --- | --- | --- | --- |
| 0–600 | Very mature or stable or inactive, low nitrogen content | yellow | yellow |
| 600–2000 | Low activity, or curing compost, or stable fertilizer | yellow-green | green |
| 2000–5000 | Very active, with high nitrogen and moderately unstable nitrogen | green | blue-green |
| 5000–20,000 | Very excessive nitrogen, potentially dangerously high | blue-green | blue |

Figure 5:
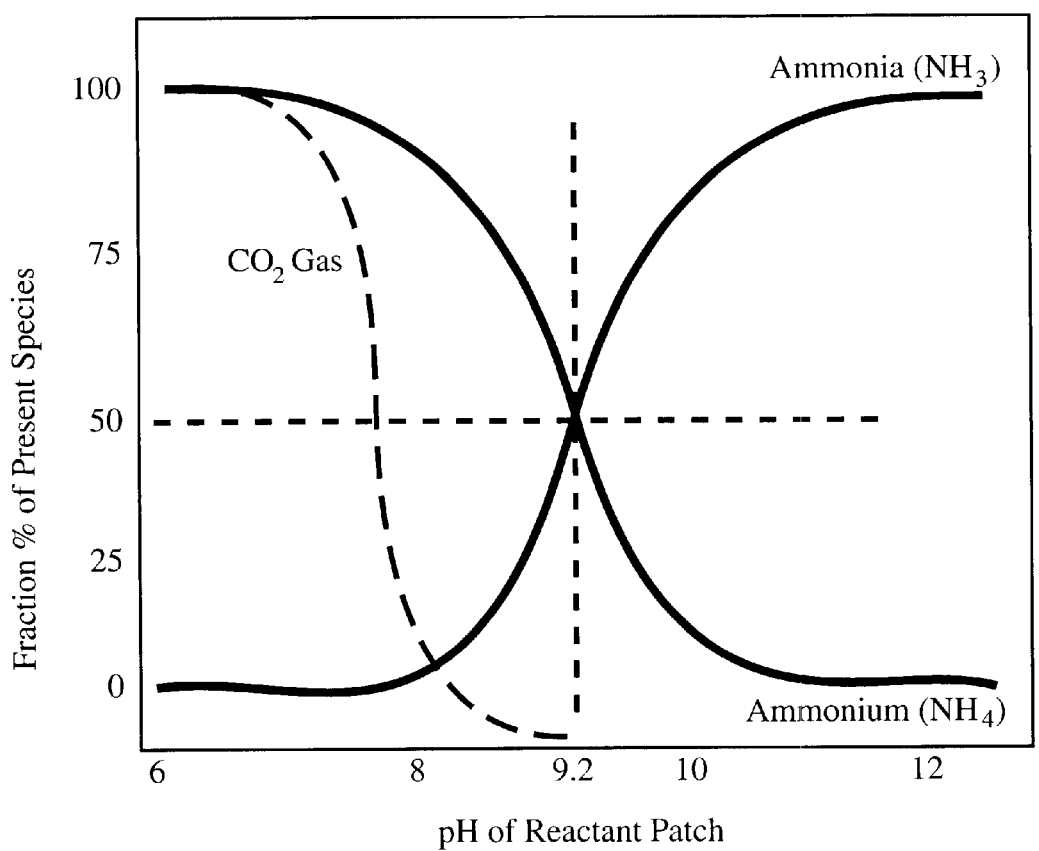
FIG. 5, is a graph, showing a relationship between pH and ionization of $NH_3$ into ammonium ionic form. The graph illustrates the basic principle upon which the invention is operative.

FIG. 5, is a graph, showing a relationship between pH and the percent of the total ammoniacial nitrogen (ammonia gas plus ammonium ion) that is present as ammonia gas, under which the invention is operative. This relationship enables the determination of ammonia content through a visual detection of the pH of the reactant patch.

The test kit may be operated in an alternative embodiment whereby the kit may be used to determine the ammonia content of the ambient air in the environment in a room where the kit has been placed. Cover 2 must be constructed such that it is gas-permeable so that diffusion of ambient air is permitted into container 1. Biological matter 5 is omitted in this embodiment whereby container 1 is empty. A calibration of the test kit in this embodiment may also be performed empirically through exposing the test kit in this embodiment to environments of known ammonia concentrations, and observing the color changes over time.

A second alternative embodiment enables the measurement of ammonia content in liquid samples, such as water, urine, or beer. In this embodiment, the biological sample 5 is a liquid, placed in container 1. The pH of the liquid sample 5 must be raised to 11.0 through the addition of a caustic solution in container 1 to convert all ammoniacal-nitrogen to ammonia gas. The ammonia gas which forms will then diffuse into the air above the liquid sample 5 in container 1. Plastic support tab 3 with reactant mass 4 is placed in the container such that the reactant mass 4 resides in the air space above the liquid sample 5. Cover 2 must be secured to form an air-tight seal. The operation of the test for ammonia content is the same as the preferred embodiment.

Features of the present invention are recited in the appended claims. The drawings herein necessarily depict specific structural and appearance features and embodiments of the test kits, and the chemical reactions, and associated color changes, useful in the practice of the present invention.

However, it will be appreciated by those skilled in the arts pertaining thereto, that the present invention can be practiced in various alternate forms, proportions, and configurations. Further, the previous detailed description of the preferred embodiment of the present invention are presented for purposes of clarity of understanding only, and no unnecessary limitations should be implied therefrom. Finally, all appropriate mechanical, chemical, and functional equivalents to the above, which may be obvious to those skilled in the arts pertaining thereto are considered to be encompassed within the claims of the present invention.

What is claimed is:

1. A test kit for determining the volatile ammonia concentration of a biological sample comprising:
   of a container;
   said container having a transparent side wall, and an open end;
   a reactant support tab;
   a reactant mass carried by said reactant support tab, said reactant mass comprising an acidic pH reactant material, and a color change indicator material; and a cover removeably and sealably engaged on said open end of said container;
      whereby the color of said reactant mass may be observed through said transparent side wall of said container;
      said acidic pH reactant material being potassium-hydrogen-phthlate.

2. The test kit for determining the volatile ammonia concentration of a biological sample, as described in claim 1, wherein said color change indicator material undergoes color changes in the pH range from about 3 to about 9, whereby said test kit can be used to test for volatile ammonia content in said container.

3. The test kit for determining the volatile ammonia concentration of a biological sample, as described in claim 1, wherein said color change indicator material comprises a first substance undergoing a color change in the pH range from about 3 to about 6, and a second substance, undergoing a color change in the pH range from about 7 to about 9, whereby said material has a range of colors from yellow to blue, depending on the pH.

4. The test kit for determining the volatile ammonia concentration of a biological sample, as described in claim 3, wherein said color change indicator material undergoes color changes in the pH range from about 3 to about 9, whereby said test kit can be used to test for volatile ammonia content in said container.

5. The test kit for determining the volatile ammonia concentration of a biological sample, as described in claim 3, wherein said color change indicator material comprises a first substance undergoing a color change in the pH range from about 3 to about 6, and a second substance, undergoing a color change in the pH range from about 7 to about 9, whereby said material has a range of colors from yellow to blue, depending on the pH.

6. The test kit for determining the volatile ammonia concentration of a biological sample, as described in claim 3, wherein said color change indicator material comprises first and second substances that exhibit different color changes in different overlapping pH ranges, whereby said substances collectively undergo a color change from yellow to green to blue in a pH range from about 3 to about 9.

7. A test kit for determining the volatile ammonia concentration of a biological sample, wherein the sample is a solid particulate biological material containing carbon dioxide and possibly ammonia in an unknown amount, said test kit comprising:
   a container having a transparent viewing wall, and an opening for introducing the sample of biological material into the container so that the sample occupies only a portion of the container interior space;
   a reactant support tab locatable within said container;
   and a reactant mass carried by said tab;
   said reactant mass comprising an acidic pH reactant material, and a color change pH indicator material that exhibits color changes in response to pH changes in said reactant material;
   means for positioning said support tab in the container so that said reactant mass is located out of contact with the same of biological material, whereby gaseous ammonia released from the biological sample is permitted to accumulate and physically contact the exposed reactant mass;
   a cover removably and sealably fitting the container opening, whereby gaseous materials released from the sample of biological material can be trapped within the container;
   said reactant support tab being positionable so that color changes in the reactant mass can be observed through said transparent viewing wall;
   said acidic pH reactant material being potassium-hydrogen-phthlate which is has an acidic buffer that chemically reacts with the released ammonia over time to produce a stablilized neutralized product having a pH related to the ammonia concentration in the reactant mass.

8. The test kit for determining the volatile ammonia concentration of a biological sample, as described in claim 7, wherein the said acidic pH reactant material comprises potassium-hydrogen phthalate.

* * * * *